United States Patent [19]
Reeve et al.

[11] Patent Number: 6,043,059
[45] Date of Patent: Mar. 28, 2000

[54] PRIMER WALKING CYCLE SEQUENCING USING PRESYNTHESIZED PRIMERS CONTAINING NUCLEOTIDE ANALOGS

[75] Inventors: Michael Alan Reeve, Henley-on-Thames; Philip Steven Robinson, Aylesbury; Stuart Ball, Loughborough, all of United Kingdom

[73] Assignee: Amersham Pharmacia Biotech UK, Buckinghamshire, United Kingdom

[21] Appl. No.: 08/981,347

[22] PCT Filed: Jun. 26, 1996

[86] PCT No.: PCT/GB96/01536

§ 371 Date: Mar. 23, 1998

§ 102(e) Date: Mar. 23, 1998

[87] PCT Pub. No.: WO97/01645

PCT Pub. Date: Jan. 16, 1997

[30] Foreign Application Priority Data

Jun. 28, 1995 [EP] European Pat. Off. .............. 95304564

[51] Int. Cl.[7] .............................. C12P 19/34; C07H 21/04
[52] U.S. Cl. .................. 435/91.1; 435/91.2; 435/810; 536/24.33
[58] Field of Search ................... 435/91.1, 91.2, 435/810; 536/24.33

[56] References Cited

U.S. PATENT DOCUMENTS 5,002,867  3/1991  Macevicz ..................................... 435/6
5,438,131  8/1995  Bergstrom et al. .................... 536/28.6

FOREIGN PATENT DOCUMENTS

4336911 A1  5/1995  Germany .
WO 90/04652  5/1990  WIPO .
WO 93/05176  3/1993  WIPO .
WO 94/06810  3/1994  WIPO .
WO 95/11970  5/1995  WIPO .

OTHER PUBLICATIONS

Ball et al., Nucleic Acids Res. 26(22), 5225–5227, 1998.
Jones et al., Nucleic Acids Res. 26(11), 2824–2826, 1998.
Hardin et al., Genome Res. 6(6), 545–550, 1996.
Azhikina et al., *Proc. Natl. Acad. Sci. USA,* vol. 90, pp. 11460–11462 (1993).
Hou et al., *Analytical Biochemistry* 221, 136–141 (1994).
Kaczorowski et al., *Analytical Biochemistry* 221, 127–135 (1994).
Kotler et al., *BioTechniques,* vol. 17, No. 3 (1994).
Shen et al., *BioTechniques,* vol. 15, No. 1 (1993).

*Primary Examiner*—Kenneth R. Horlick
*Attorney, Agent, or Firm*—Marshall, O'Toole, Gerstein, Murray & Borun

[57] ABSTRACT

A method for primer walking cycle sequencing of nucleic acid is provided using a presynthesized set of walking primers wherein the primers have a raised annealing temperature and/or improved annealing properties without increasing sequence complexity.

14 Claims, No Drawings

SEQUENCE LISTING

```
<160> NUMBER OF SEQ ID NOS: 3

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: synthesized
      nucleic acid

<400> SEQUENCE: 1
gactgttacg acttagacca tagaagatcg atagac                                    36

<210> SEQ ID NO 2
<211> LENGTH: 11
<212> TYPE: DNA
<213> ORGANISM: Artificial Sequence
<220> FEATURE:
<221> NAME/KEY: misc_feature
<222> LOCATION: (1)
<223> OTHER INFORMATION: N=5-nitroindole
<220> FEATURE:
<221> NAME/KEY: misc_feature
<222> LOCATION: (2)
<223> OTHER INFORMATION: N=5-nitroindole
<220> FEATURE:
<221> NAME/KEY: misc_feature
<222> LOCATION: (3)
<223> OTHER INFORMATION: N=5-nitroindole
<220> FEATURE:
<223> OTHER INFORMATION: Description of Artificial Sequence: synthesized
      oligonucleotide

<400> SEQUENCE: 2
nnngtcacga c                                                               11

<210> SEQ ID NO 3
<211> LENGTH: 14
<212> TYPE: DNA
<213> ORGANISM: Artificial Sequence
<220> FEATURE:
<221> NAME/KEY: misc_feature
<222> LOCATION: (1)
<223> OTHER INFORMATION: N=5-nitroindole or benzimidazole
<220> FEATURE:
<221> NAME/KEY: misc_feature
<222> LOCATION: (2)
<223> OTHER INFORMATION: N=5-nitroindole or benzimidazole or none
<220> FEATURE:
<221> NAME/KEY: misc_feature
<222> LOCATION: (3)
<223> OTHER INFORMATION: N=5-nitroindole or 5-nitroindazole or
      3-niropyrrole or benzimidazole or none
<220> FEATURE:
<221> NAME/KEY: misc_feature
<222> LOCATION: (4)
<223> OTHER INFORMATION: N=5-nitroindole or 5-nitroindazole or
      benzimidazole or none
<220> FEATURE:
<221> NAME/KEY: misc_feature
<222> LOCATION: (5)
<223> OTHER INFORMATION: N=5-nitroindole or 5-nitroindazole or
      benzimidazole or none
<220> FEATURE:
<221> NAME/KEY: misc_feature
```

```
-continued

<222> LOCATION: (6)
<223> OTHER INFORMATION: N=benzimidazole or none
<220> FEATURE:
<223> OTHER INFORMATION: Description of Artificial Sequence: synthesized
      oligonucleotide

<400> SEQUENCE: 3
nnnnnngtca cgac                                                           14
```

PRIMER WALKING CYCLE SEQUENCING USING PRESYNTHESIZED PRIMERS CONTAINING NUCLEOTIDE ANALOGS

INTRODUCTION

In primer walking sequencing, a primer/template complex is extended with a polymerase and chain terminated to generate a nested set of fragments whence the sequence is read after electrophoresis and detection (radioactive or fluorescent). A second primer is then synthesised using the sequence information near to the end of the sequence obtained from the first primer. This second ('walking') primer is then used for sequencing the same template. Primer walking sequencing is more efficient in terms of generating less redundant sequence information than the alternative 'shotgun' approach.

DISADVANTAGES OF THE CURRENT ART

The main disadvantage with primer walking is the resynthesis of the walking primer after each round of sequencing. Studier (J Kieleczawa et al, Science 258, p1787, (1992)) and others (T Azhikina et al, PNAS, 90, p11460, (1993)) have proposed elegant schemes using modular primers constructed out of presynthesised sets to avoid de novo primer synthesis after each round of sequencing. None of these walking primer schemes, however, are suited to cycle sequencing.

Cycle sequencing requires primers that have annealing temperatures near to the optimal temperature for the polymerase enzyme used for the cycle sequencing. Primers between 18 and 24 residues long are generally used for cycle sequencing.

As the length of the primer increases, then the size of any presynthesised walking primer set needed in order to achieve a given probability of obtaining a perfect match within a given number of contiguous overlapping frames also increases. For primers between 18 and 24 residues long, the size of the presynthesised walking primer set required makes primer walking an impractical proposition.

ADVANTAGES OF THE CURRENT INVENTION

The current invention allows the use of a manageably sized set of presynthesised walking primers for cycled sequencing.

THE CURRENT INVENTION

The invention provides a method for primer walking sequencing of a nucleic acid target, which method comprises performing a series of sequencing reactions, each involving hybridising a primer to the target and effecting chain extension/chain termination of the primer, wherein for each sequencing reaction there is used a primer selected from a presynthesised set of walking primers of which the annealing temperatures are raised and/or the annealing properties improved without increasing their sequence complexity.

The invention also provides a library of y oligonucleotides, where y is defined as from 2 to 20000, each oligonucleotide comprising n nucleotide residues N and x nucleotide analogue residues X wherein i) n is defined as 8 or 9,
   ii) x is defined as 3–5,
   iii) each nucleotide analogue residue X is defined as: either capable of base pairing with two or more of A C G and T, or forming stronger base interactions than A C G T,
   iv) the order of the nucleotide residues N and the nucleotide analogue residues X in the oligonucleotide is defined as: either random or the residue X at the 5'-end of the oligonucleotide chain.

A DNA sequence is herein considered as a series of contiguous overlapping identically sized frames of residues with each frame translated from the next by one residue.

The following examples will define the terminology used herein:

Let each frame be n residues long:
e.g. within the sequence
   GACTGTTACGACTTAGACCATAGMGATC-GATAGAC
   TTACGACT is a frame of 8 residues
i.e. n=8
e.g. within the sequence
   GACTGTTACGACTTAGACCATAGMGATC-GATAGAC
   TACGACT is a frame of 7 residues
i.e. n=7
Let there be i such frames suitable for selecting the walking primer
e.g. within the sequence
e.g. GACTGTTACGACTTAGACCATAGAA-GATCGATAGAC
   ACGACTTA
   TACGACTT
and TTACGACT are 3 frames of 8 residues i.e. i=3, n=8
e.g. within the sequence
   GACTGTTACGACTTAGACCATAGAA-GATCGATAGAC
   GACTTAG
   CGACTTA
   ACGACTT
and TACGACT are 4 frames of 7 residues i.e. i=4, n=7
For each frame of n residues, the number of possible sequences is given by $$4^n$$

The values of $4^n$ for n between 5 and 9 are given below

| n | $4^n$ |
|---|---|
| 5 | 1,024 |
| 6 | 4,096 |
| 7 | 16,384 |
| 8 | 65,536 |
| 9 | 262,144 |

Hence the sequence of a given 5 mer will occur about once every 1 kb on average in random sequence DNA, the sequence of a given 6 mer will occur about once every 4 kb on average, the sequence of a given 7 mer will occur about once every 16 kb on average, the sequence of a given 8 mer will occur about once every 65 kb on average and the sequence of a given 9 mer will occur about once every 262 kb on average.

Thus one would expect a given 5 mer to form a perfect match at a unique location within a template of less than about 1 kb. For templates larger than about 1 kb, the 5 mer would be expected to form perfect matches at multiple locations within the template. Such formation of perfect matches at multiple locations within the template would make the 5 mer useless as a walking primer for sequencing.

One would expect a given 6 mer to form a perfect match at a unique location within a template of less than about 4 kb. For templates larger than about 4 kb, the 6 mer would be expected to form perfect matches at multiple locations within the template. Such formation of perfect matches at multiple locations within the template would make the 6 mer useless as a walking primer for sequencing.

One would expect a given 7 mer to form a perfect match at a unique location within a template of less than about 16 kb. For templates larger than about 16 kb, the 7 mer would be expected to form perfect matches at multiple locations within the template. Such formation of perfect matches at multiple locations within the template would make the 7 mer useless as a walking primer for sequencing.

One would expect a given 8 mer to form a perfect match at a unique location within a template of less than about 65 kb. For templates larger than about 65 kb, the 8 mer would be expected to form perfect matches at multiple locations within the template. Such formation of perfect matches at multiple locations within the template would make the 8 mer useless as a walking primer for sequencing.

One would expect a given 9 mer to form a perfect match at a unique location within a template of less than about 262 kb. For templates larger than about 262 kb, the 9 mer would be expected to form perfect matches at multiple locations within the template. Such formation of perfect matches at multiple locations within the template would make the 9 mer useless as a walking primer for sequencing.

Sequencing templates and template sizes are variable and will be obvious to those skilled in the art. The following guidelines are given for example only.

Plasmid templates may be in the range 2kb to 15 kb

M13 templates may be in the range 8 kb to 15 kb

Lambda templates may be in the range 45 kb to 55 kb

Cosmid templates may be in the range 45 kb to 55 kb

Bacterial artificial chromosome templates may be in the range 50 kb to 150 kb

Yeast artificial chromosome templates may be in the range 100 kb to 1,000 kb

Thus primers of 7 residues or longer will be required in order to generate a perfect match at a unique site within plasmid and M13 templates.

Primers of 8 residues or longer will be required in order to generate a perfect match at a unique site within lambda and cosmid templates.

Primers of 9 residues or longer will be required in order to generate a perfect match at a unique site within bacterial artificial chromosome templates.

Primers of 10 residues or longer will be required in order to generate a perfect match at a unique site within yeast artificial chromosome templates.

For primer walking sequencing using a presynthesised set of walking primers, it is possible to calculate the probability of finding a perfect match between a primer within the presynthesised set and one of the sequences within i contiguous overlapping frames of n residues near to the end of the sequence read from the previous primer.

Let S be the number of primers n residues long comprising the set of walking primers For a single frame n residues long, the probability that there will be a perfect match between the frame sequence and a primer n residues long in the set of walking primers is given by $$S/4^n$$

For a single frame n residues long, the probability that there will not be a perfect match between the frame sequence and a primer n residues long in the set of walking primers is given by $$1-(S/4^n)$$

For i contiguous overlapping frames n residues long, the probability that there will not be a perfect match between any of the frame sequences and a primer n residues long in the set of walking primers is given by $$P=(1-(S/4^n))^i$$

Thus $$\log P = i \log(1-(S/4^n))$$

$$i = \log P / \log(1-(S/4^n))$$

$$S = 4^n(1-(P)^{1/i})$$

$$S/4^n = (1-(P)^{1/i})$$

The following table values give the fraction of the walking primer set needed to give the percentage probability (P) shown of a perfect match within the number of contiguous overlapping frames (i) shown.

| | $S/4^n =$ | | | |
| --- | --- | --- | --- | --- |
| | | P | | |
| i | 80% | 90% | 99% | 99.9% |
| 5 | 0.275 | 0.369 | 0.602 | 0.749 |
| 10 | 0.149 | 0.206 | 0.369 | 0.499 |
| 20 | 0.077 | 0.109 | 0.206 | 0.292 |
| 50 | 0.032 | 0.045 | 0.088 | 0.129 |
| 100 | 0.016 | 0.023 | 0.045 | 0.067 |
| 200 | 0.008 | 0.011 | 0.023 | 0.034 |
| 500 | 0.003 | 0.005 | 0.009 | 0.014 |

The number of 5 mers needed in order to give the percentage probability (P) shown of a perfect match within the number of contiguous overlapping frames (i) shown is given in the following table:

| | P | | | |
| --- | --- | --- | --- | --- |
| i | 80% | 90% | 99% | 99.9% |
| 5 | 282 | 378 | 616 | 767 |
| 10 | 153 | 211 | 378 | 511 |
| 20 | 79 | 112 | 211 | 299 |
| 50 | 33 | 46 | 90 | 132 |
| 100 | 16 | 24 | 46 | 69 |
| 200 | 8 | 11 | 24 | 35 |
| 500 | 3 | 5 | 9 | 14 |

The number of 6 mers needed in order to give the percentage probability (P) shown of a perfect match within the number of contiguous overlapping frames (i) shown is given in the following table:

| | P | | | |
| --- | --- | --- | --- | --- |
| i | 80% | 90% | 99% | 99.9% |
| 5 | 1126 | 1511 | 2466 | 3068 |
| 10 | 610 | 844 | 1511 | 2044 |
| 20 | 315 | 446 | 844 | 1196 |
| 50 | 131 | 184 | 360 | 528 |

-continued

| | P | | | |
|---|---|---|---|---|
| i | 80% | 90% | 99% | 99.9% |
| 100 | 66 | 94 | 184 | 274 |
| 200 | 33 | 45 | 94 | 139 |
| 500 | 12 | 20 | 37 | 57 |

The number of 7 mers needed in order to give the percentage probability (P) shown of a perfect match within the number of contiguous overlapping frames (i) shown is given in the following table:

| | P | | | |
|---|---|---|---|---|
| i | 80% | 90% | 99% | 99.9% |
| 5 | 4506 | 6046 | 9863 | 12272 |
| 10 | 2441 | 3375 | 6046 | 8176 |
| 20 | 1262 | 1786 | 3375 | 4784 |
| 50 | 524 | 737 | 1442 | 2114 |
| 100 | 262 | 377 | 737 | 1098 |
| 200 | 131 | 180 | 377 | 557 |
| 500 | 49 | 82 | 147 | 229 |

The number of 8 mers needed in order to give the percentage probability (P) shown of a perfect match within the number of contiguous overlapping frames (i) shown is given in the following table:

| | P | | | |
|---|---|---|---|---|
| i | 80% | 90% | 99% | 99.9% |
| 5 | 19022 | 24183 | 39453 | 49086 |
| 10 | 9765 | 13500 | 24183 | 32702 |
| 20 | 5046 | 7143 | 13500 | 19137 |
| 50 | 2097 | 2949 | 5767 | 8454 |
| 100 | 1049 | 1507 | 2949 | 4361 |
| 200 | 524 | 721 | 1507 | 2228 |
| 500 | 197 | 328 | 590 | 918 |

The number of 9 mers needed in order to give the percentage probability (P) shown of a perfect match within the number of contiguous overlapping frames (i) shown is given in the following table:

| | P | | | |
|---|---|---|---|---|
| i | 80% | 90% | 99% | 99.9% |
| 5 | 72090 | 96731 | 157811 | 196346 |
| 10 | 39059 | 54002 | 96731 | 130810 |
| 20 | 20185 | 28574 | 54002 | 76546 |
| 50 | 8389 | 11796 | 23069 | 33817 |
| 100 | 4194 | 6029 | 11796 | 17564 |
| 200 | 2097 | 2884 | 6029 | 8913 |
| 500 | 786 | 1311 | 2359 | 3670 |

The following example clearly shows that only a fraction of the complete set of presynthesised walking primers of length n residues needs to be used in order to have a very high probability of finding a perfect match between one of the presynthesised walking primers and one of i contaguous overlapping frames of n residues where i is smaller than the average length of sequence read per cycle (about 400–500 bases).

For this example, the number (i) of contiguous overlapping frames of 8 mers (n=8) needed in order to give the percentage probability (P) shown of a perfect match for a set of presynthesised walking primers of size S is given in the following table:

| | i for . . . | | |
|---|---|---|---|
| S | 90% probability of finding a perfect match | 99% probability of finding a perfect match | 99.9% probability of finding a perfect match |
| 100 | 1494 | 2988 | 4482 |
| 500 | 298 | 596 | 894 |
| 1000 | 148 | 296 | 444 |
| 1500 | 99 | 198 | 297 |
| 2000 | 74 | 148 | 222 |
| 3000 | 49 | 98 | 147 |
| 4000 | 36 | 72 | 108 |
| 5000 | 29 | 58 | 87 |

Thus, for example, a presynthesised set of 1,500 8 mers would give a 90% chance of finding a perfect match between one of the 8 mers and one of 99 contiguous overlapping frames 8 residues long.

The same presynthesised set of 1,500 8 mers would give a 99% chance of finding a perfect match between one of the 8 mers and one of 198 contiguous overlapping frames 8 residues long.

The same presynthesised set of 1,500 8 mers would give a 99.9% chance of finding a perfect match between one of the 8 mers and one of 297 contiguous overlapping frames 8 residues long.

In the above example, such a presynthesised set of walking primers would allow a very high probability of selecting an 8 mer presynthesised walking primer after each round of sequencing. A set of 1,500 8 mers is a manageable amount for synthesis and accessing for each round of priming. Such 8 mer primers would also be expected to generate a perfect match at a unique site within all templates of a size up to and including lambda and cosmid templates. Such simple 8 mer primers would not, however, be suitable for cycle sequencing. As stated above, cycle sequencing requires primers that have annealing temperatures near to the optimal temperature for the polymerase enzyme used for the cycle sequencing. Primers between 18 and 24 residues long are generally used for cycle sequencing.

The current invention relies upon raising the annealing temperature (or, more generally, improving the annealing properties) of a presynthesised set of walking primers (of the type described above) WITHOUT increasing the size of the walking primer set required in the following ways:

A. Adding residues to the primers that are capable of base pairing with each of the four DNA bases (A, C, G and T). Examples are:

i) inosine:

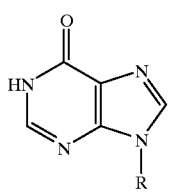

(which pairs with all four bases with the preference C>A>G~T).

ii) 5-nitro indole:

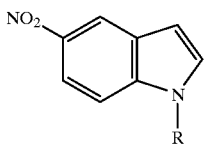

(which can pair with all four bases, but mainly stabilises by favourable stacking interactions).

iii) 5-nitro-pyrrole:

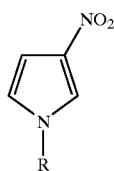

(which pairs with all four bases, but mainly stabilises by favourable stacking interactions).

iv) K (2-amino-6-methoxyaminopurine):

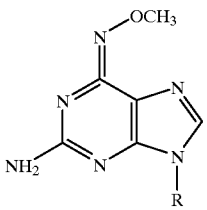

(which pairs with pyrimidines).

v) P (6H,8H-3,4-dihydropyrimido[4,5-c][1,2]oxazin-7-one):

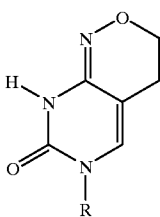

(which pairs with purines).

vi) Others that may be used which are obvious to those skilled in the art. B. Using bases in the primers that form stronger base pairing interactions than the normal A, C, G and T bases. Examples are:

i) 2-aminoadenine

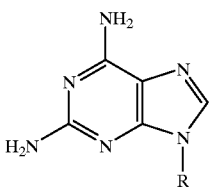

(which can be used in place of A).

ii) 5-methylcytosine

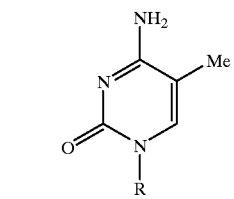

(which can be used in place of C).

iii) Others that may be used which are obvious to those skilled in the art.

The bases listed above may be collectively termed degenerate bases. The number of such degenerate bases, in the walking primers of the pre-synthesised set with which the invention is concerned, is preferably from 1 to 20. These degenerate bases may be interspersed along the length of each oligonucleotide walking primer, or may be concentrated, at the 5'-end, or at the 3'-end, or in the middle. Good results have been obtained using 3, 4 or 5 degenerate bases concentrated at the 5'-end of the oligonucleotide.

EXAMPLE 1

The following oligonucleotides were synthesised:

5'GTCACGAC 3' (AM1)

5'XXX GTCACGAC 3' (AM2)

where X denotes a 5-nitroindole residue.

25 pmol of each of these primers were added to CsCl purified M13mp8 template and cycle sequenced on a Vistra DNA Systems DNA Labstation 625 (Amersham International plc.) using the Labstation Thermo Sequenase™ fluorescent dye-terminator cycle sequencing kit (RPN2435, Amersham International plc.), the Labstation FMP™ fluorescent dye-terminator precipitation kit (RPN2433, Amersham International plc.) and the 1–32 dye-terminator cycle sequencing, v2.0 method. The method was edited for this example by reducing the cycle sequencing annealing temperature to 40° C. followed by 2 sec/° C. ramping to the 4 minute extension at 60 degrees.

The samples were then electrophoresed and analysed on an Applied Biosystems 373A fluorescent sequencer.

The results clearly showed a marked improvement in both the signal strength and sequence quality by virtue of the added 5-nitroindole residues at the 5' end of primer AM2. Signal strength was 8 times higher with AM2 than with AM1. Readable sequence was 460–500 bases with AM2 compared to 340–380 with AM1.

EXAMPLE 2

Oligonucleotides were synthesised of general formula

5' $X_1X_2 \ldots X_m$GTCACGAC 3' as follows

| X | m |
|---|---|
| 5-nitroindole | 1, 2, 3, 4, 5 |
| 5-nitroindazole | 3, 4, 5 |
| 3-niropyrrole | 3 |
| benzimidazole | 1–6 |

The oligonucleotides containing 5-nitroindole residues all performed better than AM1, in the test described in Example 1, with those where m was 3 or 4 being marginally the best.

The performance of the oligonucleotides containing 5-nitroindazole residues were comparable to AM2.

The performance of the oligonucleotide containing 3-nitropyrrole residues was better than AM1 (the signal was twice as strong).

On the basis of these results, it can be predicted that a library of presynthesised oligonucleotides, containing 8 or 9 ordinary bases and 3, 4 or 5 degenerate bases particularly those listed above, will give improved results when used in a primer walking sequencing method as described herein.

We claim:

1. A method for primer walking sequencing of a nucleic acid target on a template strand, which method comprises performing a series of sequencing reactions, each involving hybridising a primer to the target and effecting chain extension/chain termination of the primer, wherein for each sequencing reaction there is used a primer which is a single covalently linked oligonucleotide selected from a presynthesised set of walking primers wherein each walking primer consists of a chain of nucleotide residues and at least one nucleotide analogue residue whereby the annealing temperatures of the primer to the target are raised and/or the annealing properties of the primer to the target are improved without increasing their sequence complexity wherein the walking primers contain bases capable of pairing with any of the four bases on the template strand.

2. A method according to claim 1 wherein the nucleic acid target is cycle sequenced.

3. A method according to claim 1 wherein fluorescent dye-terminator labelling is used for sequence detection.

4. A method according to claim 1 wherein radioactive-ddNTP labelling is used for sequence detection.

5. A method according to claim 1 wherein the walking primers contain contiguous bases at their 5' ends, the said bases being capable of pairing with any of the four bases on the template strand.

6. A method according to claim 1 wherein the walking primers contain interspersed bases throughout their sequence, the said bases capable of pairing with any of the four bases on the template strand.

7. A method according to claim 5 wherein the said bases capable of pairing with any of the four bases on the template strand are inosine.

8. A method according to claim 5 wherein the said bases capable of pairing with any of the four bases on the template strand are 5-nitroindole.

9. A method according to claim 5 wherein the said bases capable of pairing with any of the four bases on the template strand are 3-nitropyrrole.

10. A method according to claim 5 wherein the said bases capable of pairing with any of the four bases on the template strand are a mixture of K (2-amino-6-methoxyaminopurine) and P (6H,8H-3,4-dihydropyrimido[4,5-c][1,2]oxazin-7-one).

11. A method according to claim 5 wherein the said bases capable of pairing with any of the four bases on the template strand are combinations of bases selected from the group consisting of inosine, 5-nitroindole, 3-nitropyrrole, K (2-amino-6-methoxyaminopurine) and P (6H,8H-3,4-dihydropyrimido[4,5-c][1,2]oxazin-7-one).

12. A library of y oligonucleotide chains, where y is defined as from 2 to 20000, each oligonucleotide chain comprising n nucleotide residues N and x nucleotide analogue residues X and having a 5' end wherein i) n is defined as 8 or 9, ii) x is defined as 3–5, iii) (n+x) is defined as 12 to 14 iv) each nucleotide analogue residue X is defined as: either capable of base pairing with two or more of A C G and T, or forming stronger base interactions than A C G T, v) the order of the nucleotide residues N and the nucleotide analogue residues X in the oligonucleotide is defined as: either random or comprising a residue X at the 5'-end of the oligonucleotide chain.

13. A sequencing kit for a nucleic acid target comprising a polymerase enzyme, nucleotide triphosphates, chain terminating nucleotide triphosphate analogues, reaction buffer, together with a presynthesised set of walking primers wherein each walking primer is a single covalently linked oligonucleotide consisting of a chain of nucleotide residues and at least one nucleotide analogue residue whereby the annealing temperatures of the primer to the target are raised and/or the annealing properties of the primer to the target are improved without increasing their sequence complexity.

14. A sequencing kit according to claim 13 wherein a library of y oligonucleotide chains is used as the presynthesized set of walking primers where y is defined as from 2 to 20000, each oligonucleotide chain comprising n nucleotide residues N and x nucleotide analogue residues X and having a 5' end wherein i) n is defined as 8 or 9, ii) x is defined as 3–5, iii) (n+x) is defined as 12 to 14 iv) each nucleotide analogue residue X is defined as: either capable of base pairing with two or more of A C G and T, or forming stronger base interactions than A C G T, v) the order of the nucleotide residues N and the nucleotide analogue residues X in the oligonucleotide is defined as: either random or comprising a residue X at the 5'-end of the oligonucleotide chain.

* * * * *